| United States Patent [19] | [11] Patent Number: 4,861,715 |
| Bergter et al. | [45] Date of Patent: Aug. 29, 1989 |

[54] PROCESS FOR THE PRODUCTION OF NOURSEOTHRICINE AND ITS ADSORBATE

[75] Inventors: Friedrich Bergter; Harald Bocker; Ernst-Joachim Bormann; Wolfgang Forberg; Heinz Fricke; Udo Gräfe; Hans-Helmut Grosse; Ingeborg Heller; Matthias Hilliger; Wolf Junne; Hellmut Linde, all of Jena; Michael Menner, Ammerbach; Klaus-Dieter Menzel, Apolda; Peter-Jürger Müller, Ammerbach; Gunter Plonka, Jena; Hans D. Pohl, Jena; Jörg Schneider, Jena; Heinz Thrum, Jena, all of German Democratic Rep.

[73] Assignee: VEB Jenapharm, Jena, German Democratic Rep.

[21] Appl. No.: 572,928

[22] Filed: Jan. 20, 1984

[30] Foreign Application Priority Data

Jan. 20, 1983 [DD] German Democratic Rep. ............... 2473707
Sep. 28, 1983 [DD] German Democratic Rep. ............... 2552658
Oct. 25, 1983 [DD] German Democratic Rep. ............... 2559431
Oct. 25, 1983 [DD] German Democratic Rep. ............... 2559464
Oct. 25, 1983 [DD] German Democratic Rep. ............... 2559465
Oct. 25, 1983 [DD] German Democratic Rep. ............... 2559448

[51] Int. Cl.$^4$ .................. C12P 21/02; C12P 1/04
[52] U.S. Cl. ........................ 435/70; 435/170
[58] Field of Search ................... 435/70, 170

[56] References Cited

U.S. PATENT DOCUMENTS 3,965,002  6/1976  Magnusson .................. 210/713

OTHER PUBLICATIONS

Martin and Demain, "Control of Antigiotic Brosynthesis"; *Microbiological Reviews*, vol. 44, No. 2, pp. 230-251 (1980).

*Primary Examiner*—Jerome D. Goldberg
*Assistant Examiner*—Joseph A. Lipovsky
*Attorney, Agent, or Firm*—Michael J. Striker

[57] ABSTRACT

A process is disclosed for the fermentative production of the ergotropically effective antibiotic nourseothricin, with which, using different carbohydrate sources and suitable inorganic and organic nitrogen sources as well as different mineral salts, with or without addition of stock substances of the respiratory chain or the intracellular amino acid transport, and through influencing the phosphate substance exchange and avoidance of further limitations with regulated acidity conditions, high concentrations of this antibiotic are cultivated in the culture solution. The recovery of the active substance in the culture solution follows either by chromatographic techniques in the form of salts or through addition of a physiologically compatible adsorbent as mycelium-containing nourseothricin-adsorbate, which preferably can be added to the dosaging of mixed feed agents.

11 Claims, 6 Drawing Sheets

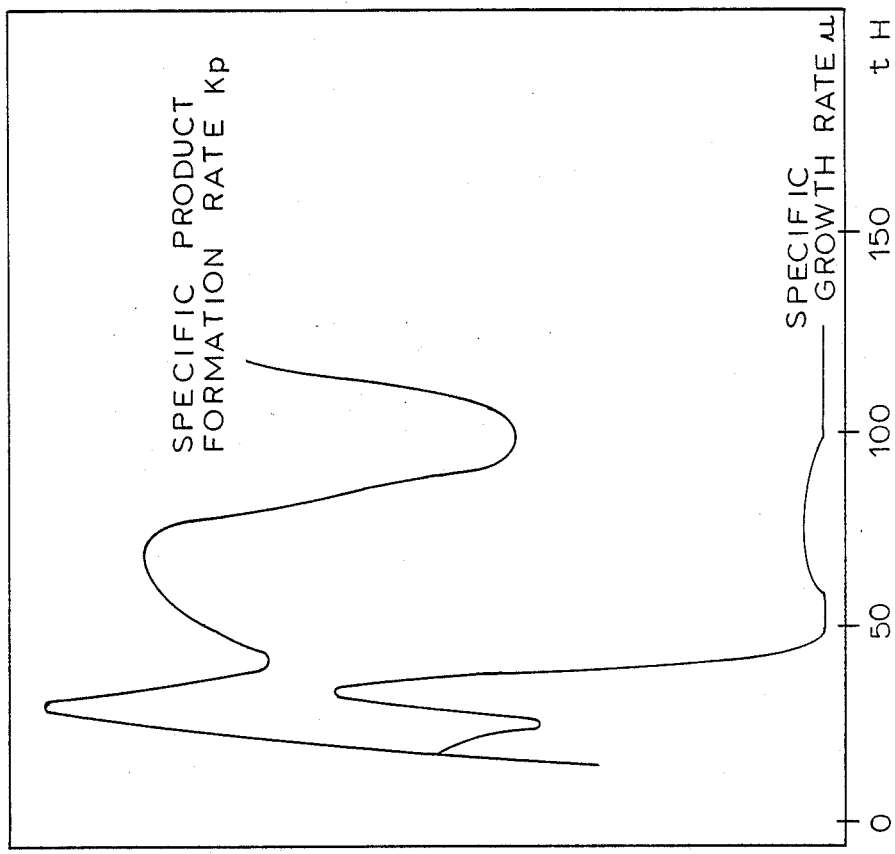
FIG. 7
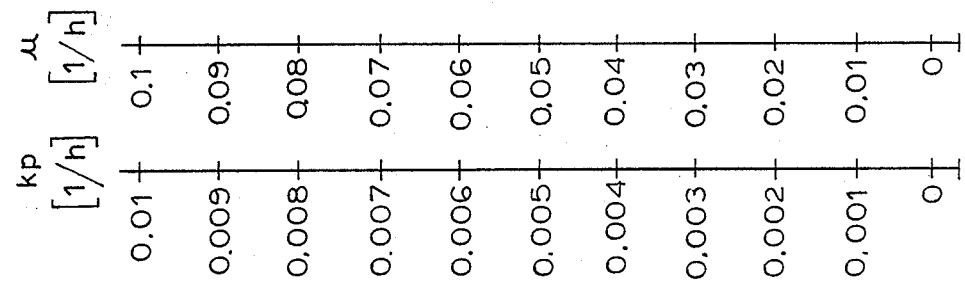

PROCESS FOR THE PRODUCTION OF NOURSEOTHRICINE AND ITS ADSORBATE

BACKGROUND OF THE INVENTION

The invention concerns a new process for the fermentative production of nourseothricin and its recovery in the form of its salts and adsorbates. Nourseothricin is an antibiotic belonging to the group of streptothricines, which after delivery in ergotropic doses with animal feed upon agricultural utilization effects an accelerated increase in living matter as well as simultaneously a decrease in feed expense. It is thereby of use for animal production as well as the pharmaceutical and mixed feed agent industries.

The antibiotic nourseothricin, isolated from the culture of a variety of streptomycae noursei ATCC 11455, is effective in vitro against Gram-positive and Gram-negative bacteria as well as against mycobacteria (Bradler, G. and H. Thrum: Nourseothricin A and B, two new antibacterial antibiotics of a Streptomycae-Noursei variation. Zschr. Allgem. Mikrobiol. 3, 105–112 (1963)). Nourseothricin is a base soluble in water and lower alcohols. Easily manageable forms are its salts. The molecule of nourseothricin is constructed from the amino sugar gulosamine and the amino acids streptolidine and $\beta$-lysine. The individual components of nourseothricin distinguish by the number of peptide-like $\beta$-lysine groups connected with one another in the molecule. The nourseothricin complex is composed of about 90% to approximately the same portions of both main components F and D as well about 10% of both by-components C and E (Gräfe, U.; Bocker, H.; Reinhardt, G. und H. Thrum: Regulative Beeinflussung der Nourseothricinbiosynthese durch o-Aminobenzoesäure in Kulturen des Streptomyces noursei JA 3890b. Zschr. Allg. Mikrobiol. 14, 659–675 (1974)).

The Streptomycete stock forming the antibiotic Nourseothricin is placed under the designation Streptomyces noursei ZIMET JA 3890b in the Stammsammlung des Zentralinstitute für Mikrobiologie und experimentelle Therapie der Akademie der Wissenschaften der DDR and now carries the designation Streptomyces noursei ZIMET 43716.

According to the processes known from literature (Bocker, H. and H. Thrun: Stimulation of nourseothricin produced by aminobenzoic acids. In: Herold, M. and Z. Gabriel: Antibiotics—Advances in research, production and clinical use. London 1966; p. 584–587) the cultivation follows under aerobic conditions. For this purpose spore material of this Streptomyces stock, lyophilically dried in soil, is applied to suitable agar nutrient base. After 6–10 days incubation at 28°–30° C., the so grown sporulated mycelium grass is used for inocculation of liquid sterile nutrient media. The inocculation can also follow directly with a preserve of submersed mycelium of the nourseothricin-forming Streptomycete stock, lyophilically dried in gelatin. The liquid nutrient media for the submersed cultivation of the inocculation material contains as substrate carbon and nitrogen sources as well as inorganic salts. As carbon sources, glucose and/or glycerine are employed. As nitrogen sources, particularly soy meal, various amino acids and/or ammonium salts come into consideration. The most favorable acidity for the cultivation of the inocculation material at the start of cultivation lies in the range of pH 6.0 up to 6.7.

The incubation follows at temperatures from 28° to 30° C. over a time period of 24 to 48 hours. The so provided inoculation material serves for the inocculation of sterile liquid nutrient media for the main culture. Such nutrient media are composed of carbon and nitrogen sources as well as inorganic salts. As carbon sources, cornstarch and/or glucose are employed. As nitrogen sources, particularly soy meal, various amino acids and/or ammonium salts come into consideration. The most favorable acidity for the antibiotic formation at the start of fermentation lies in the range of pH 6.0 up to pH 7.5. The cultivation follows at temperatures of 26°–32° C., preferably from 28° to 30° C., up to 150 hours.

The submersed cultivation of Streptomyces noursei ZIMET JA 3890b follows in known manner as a so-called vibration culture, or instead in aerated fermenters, without dosing of substrate or regulation of the pH-value.

It is known (Bradler, G. and H. Thrum: Nourseothricin A und B, zwei neue antibakterielle Antibiotika einer Streptomyces-noursei-Variante. Zschr.Allgem.Mikrobiol. 3, 105–112 (1963)) that the relatively small nourseothricin formation in the original fermentation medium can be increased approximately 5 to 10 times through the addition of aminoarylcarboxylic acids, particularly of 5–10 mM o-aminobenzoic acid, added at the start to the main culture, under the known technical conditions (Bocker, H. and H. Thrum: Stimulation of nourseothricin production by aminobenzoic acids. In: Herold, M. and Z. Gabriel: Antibiotics—Advances in research, production and clinical use. London 1966, p. 584–587). It is known from tests (summarized and cited in Gräfe, U.; Steudel, A.; Bocker, H. and H. Thrum: Regulative influence of o-aminobenzoic acid (OABA) on the biosynthesis of nourseothricin in cultures of Streptomyces noursei JA 3890b. V. Effect of OABA on cytochrom levels and amino acid transport. Zschr.Allgem.Mikrobiol. 30, 185–194 (1980)) that o-aminobenzoic acid and/or other aminoarylcarboxylic acids specifically regulate the formation of cytochrome of the a-type (cytochrome-oxydase) and thereby indirectly inhibits not only the amino acid transport from the nutrient medium into the mycelium but also the oxidative desamination of the amino acids in the cells of the nourseothricin-former. Hereby is avoided on the one hand the repression of the secondary material exchange by means of a cellular over-supply of nitrogen catabolites. On the other hand, it is in this manner prevented that amino acids of the medium, serving as precursors of the nourseothricin, are extensively consumed by the antibiotic-former during its growth phase. These amino acids are thereby better available to the secondary material exchange in the course of the nourseothricin formation, since preferably the inorganic nitrogen source (ammonium nitrogen) is used for the biomass formation.

The fermentative nourseothricin production using aminoarylcarboxylic acids, which to known extent indeed make possible a substantial increase in the fermentation yield, displays however disadvantages, particularly with regard to cost, sterilization and waste water problems, which oppose a large-scale technical employment.

It is moreover known that the biosynthesis of most secondary metabolites is negatively influenced by excessive phosphate (summarized in: Martin, J. F. and A. L. Demain: Control of antibiotic biosynthesis. Microbiol. Rev. 44, 230–251 (1980)), technical microbial fermentations for the production of secondary metabolites, for example antibiotics, are performed with phosphate concentrations that are sub-optimal for the growth of the former. As a rule, complex nutrient base components of plant and animal origin, such as starch, soy meal, corn spring water, molasses, meat extracts, among others, are employed for fermentations of technical scale for the recovery of secondary metabolites. Indeed according to construction and pretreatment, such complex nutrient base components possess different contents of total phosphate of different biological availability. A portion of the available phosphate is provided in the fermentation media as soluble phosphate. This fact substantially complicates the standardization of the nutrient media.

The starting concentrations of soluble or available phosphate have, however, a different significance for the fermentative yield of the desired secondary metabolite, since on the one hand a determined amount of phosphate is necessary for the growth of the producing microorganisms and, on the other hand, too high phosphate starting concentrations inhibit the secondary metabolite formation.

The patent DD 155239 claims the use of concentration of the phosphate ions contained in the culture medium as a regulating measure for stabilization of the cultivation process. The process refers, however, only to the fermentative recovery of biomass, whereby the nominal value of the concentration is adjusted within the range from 20 to 60 mg/l phosphorus. The use of this process is not known for the regulation of biosynthesis of secondary metabolites in microbial batch-cultures.

With the improvement of microbial production techniques for the production of secondary metabolites, the nutrient medium and the producing microorganisms are so adapted to one another by means of mutual modifications that a compromise between both opposing regulative influences of the phosphate takes place. In this manner the step-wise increase in efficiency is, however, time-expensive and cost-intensive.

It is known, moreover, that in addition to the regulative influence by means of the composition of the nutrient medium, an improvement in the fermentative yield can also be obtained by means of a control of the fermentation process, preferably as a real-time control (Sukatsch, D. A. and G. Nesemann: Automatische Parametererfassung bei industriellen Fermentationen. Chemie-Technik 6, 261–265 (1977)).

With the use of real-time control necessary for an effective fermentation performance, there is present the difficulty of having to modulate the continuously measurable global process parameters, stabilizing in the fermentation techniques, such as pH-value, $pO_2$-value, dosage rate, exhaust gas composition, heat formation, instead of first by means of mainly time-expensive chemical analysis, subsequently determined substrate concentrations as primary regulative process parameter.

With regard to the isolation of the nourseothricin, it is known that the active substance is adsorbed in suitable cation exchangers from the culture filtrate freed of mycelium, is subsequently eluted with dilute acids, and after neutralization, concentration of the eluate, repeated precipitation of the crude product in the system methanol/acetone, and drying, and then obtained as pure substance (Bradler, G. and H. Thrum: Nourseothricin A und B, zwei neue antibakterielle Antibiotika einer Streptomyces-noursei Variante. Zschr.Allgem.-Mikrobiol. 3, 105–115 (1963)).

SUMMARY OF THE INVENTION

The aim of the present invention is to provide the active substance nourseothricin in higher space-time-yield.

The invention is therefore based upon the object of providing a technically favorable process which, avoiding the disadvantages of the previously known processes, makes possible the industrial production of nourseothricine in the form of its salts and adsorbates.

It has been found that addition of stock material of the respiratory chain, for example sodium azide or other alkali azides, pyrocatechol, as well as Amytal (=ethylisoamylbarbituric acid) and/or stock material of the amino acid transport in living cells, for example β-alanine or water-soluble zinc salts, added to the main culture from the time point of the inocculation, provides a promoting activity on the biosynthesis of nourseothricin, without influencing in an altering manner the chemical and biological characteristics of the fermentation process.

An addition of inhibitors of the respiratory chain and/or the amino acid transport can be avoided, when stock of higher amylolytic activity is used and polymer carbon sources, mainly cornstarch, are added.

Surprisingly, it has been discovered that the metabolic activity of the nourseothricin-forming cultures (respiration, rate of oxygenation, glucose and ammonium withdrawal, antibiotic formation, among others) is determined primarily through the specific availability of the phosphate in the course of the fermentation and not solely by the supply of carbon and nitrogen sources. Therewith it is of particular significance that generally the starting concentrations of soluble and also of biologically available phosphate in the sterilized nutrient medium are lowered by performing the thermal sterilization on the basis of a sterilization functional, of the content of sulfate ions and of inorganic salts or metal ions, which provide difficultly soluble sediment with phosphate and sulfate ions. Therewith it has been shown that for the lowering of the starting concentration in the case of the presence of a sufficient amount of sulfate ions the shift of acidity of the weakly acid nutrient medium to the alkaline pH-values in the course of the sterilization by means of precipitation of calcium sulfate and the therewith connected removal of acid sulfate ions from the medium is responsible. Thereafter the starting concentration of soluble or biologically available phosphates is also lowered by means of adjustment of an alkaline pH-value before the sterilization. The increase of the pH-value effects in such manner that conditions for the precipitation of the phosphate as a difficultly soluble sediment with determined, metal ions provided in the nutrient medium, are provided. The precipitation of the phosphate-containing sediment is promoted by means of the select addition of such metal ions, for example of zinc(II) and/or iron(III), aluminum(III), magnesium(II), calcium(II), manganese(II), among others. Particularly favorable for a phosphate precipitation is the sterilization method employed with most technical fermentations, with directly acting pressurized steam, as well as the presence of calcium carbonate, which is added for pH-buffering of the fermentation.

The phosphate content of the medium can generally also be lowered by means of decreasing the portion of phosphate-containing complex starter material. Thereby the process is made more cost-favorable.

Under the described prerequisites the phosphate starting concentration of dissolved or biologically available phosphates is so lowered that the specific upper tolerance value of the phosphate for the nourseothricin-producing microorganisms is not exceeded. These low phosphate concentrations offer the possibility of obtaining an extensively standardized medium by means of a defined phosphate supply after the sterilization. In other respects the phosphate-material exchange of the microorganisms can be so controlled through the addition regime of the phosphate, that a high product yield is obtained. The supply of phosphate can be performed in the form of a solution or a solid or a suspension. The phosphate can be present either as free phosphate ions or as chemically or physically bound phosphate. According to the specific fermentation regime, the supply of phosphate or phosphate-containing substances follows after the sterilization or during the fermentation by means of a single and/or multiple and/or continuous addition. The continuous addition can be performed with different rates during the fermentation.

This addition follows additively to the nascent phosphate in the culture solution from the complex phosphate sources, for example soy meal, peanut meal, potato starch, among others, through hydrolytical or enzymatic treatment or through reversible setting-free from inorganic sediments. The hydrolytic treatment of the previously mentioned organic substrate is promoted by means of sterilization with alkaline reaction. By means of an increase in the hydrogen ion concentration in the course of the fermentation within the physiological range is attained a stimulation of the metabolic activities through a better setting-free of phosphate from inorganic sediment.

As a boundary condition, it must be certain that no limitations of substrate unfavorable for the product formation, and no growth or increased material exchange activity resulting from environmental conditions in connection with the phosphate supply, are provided.

After alkaline sterilization in the pH-value range from 7.4 to 7.8, with conclusion of the sterilization and attainment of a pH-value range from 7.2 to 8.8, it has moreover been found that upon control of the fermentation process by means of adjustment and maintenance of a ratio of glucose to inorganic nitrogen from 5 to 15 to 0.015 to 0.2 (g/l glucose:g/l inorganic nitrogen) by means of dosing of glucose and ammonium salt or ammonium hydroxide in the acidity range of pH 5.0 to 6.5 and an oxygen partial pressure ($pO_2$) from 30 to 80%, preferably 40 to 60%, the productivity of the nourseothricin formation is favorably influenced over a longer period of time.

Surprisingly, it has been found that the choice of the appropriate nominal value interval for the regulation of the pH-value of the culture solution in the range of physiologically-regulative effective pH-value upon dosing of a suitable concentrated ammonium hydroxide solution to guarantee the lower pH-limit, results in a situation wherein the time course of the ammonium hydroxide dosing rate describes the time course of the consumption rate of the physiologically active phosphate. The described criterion depends upon the determination of the lower regulation limit of the pH-value. The pH-course in the first hours of fermentation, and therewith the setting in of the ammonium hydroxide dosing rate are determined by means of the buffering of the starting nutrient medium.

Therewith is available a continuous signal of good sensitivity for the control of the direct and/or indirect phosphate dosaging and therewith for the control of the metabolic activity of the fermentation culture.

With regard to direct phosphate dosaging, in the form of the addition of phosphate-containing substances from an extreme reservoir and the indirect phosphate dosaging as preparation of phosphate compounds through enzymatic or hydrolytic treatment of more complex substrate, it has been found that the conduct of the ammonium hydroxide dosaging rate passover between direct and indirect phosphate dosaging is indicated through significant increase or drop. The size of the change is determined by means of the phosphate afterflow.

It has been moreover been found that the actual ammonium hydroxide dosaging rate serves as control parameter for the dosaging of carbon sources as well as further nitrogen sources and substances with effector activity, and under consideration of the specific oxygen transfer rate of the fermenter involved the direct phosphate dosaging is so to be changed that the fermentation proceed with more favorable product formation rate. In this manner one succeeds, under the reactor-technical provided oxygen starting conditions, with defined amount of air supply, with the realization of a high product final value, the effective utilization of the substrate in the desired fermentation time period, and the limiting of the biomass concentration to a preparation-technically representable extent.

In addition, it has been determined that the time course of the metabolic activity is described by the reaction heat and/or the respiration rate. For this reason the actual reaction heat and the respiration are likewise control parameters for the dosaging of phosphate or other substances.

For the production processes, nourseothricin-forming Streptomyceten stock of the class Streptomyces, particularly of the type Streptomyces noursei, is suitable, which is characterized by the following criteria:
sensitivity of the nourseothricin-formation against high concentrations of soluble phosphate in the nutrient medium of the main culture
capacity of the treatment for complex phosphate-containing carbon and nitrogen sources
amylolytic activity to the treatment of polymeric carbon sources.

The concrete performance of the described process adjusts itself accordingly to the extent that the always employed Streptomyceten stock is arranged with regard to these three criteria.

So in the scope of the process in a limiting case with high phosphate sensitivity of the producers, a high nourseothricine formation is only then possible when the starting concentration of soluble phosphate in the nutrient medium of the main culture is dropped into the range below 10 mg/l phosphate-phosphorus by means of the previously described measures, such as heat sterilization in the alkaline milieu and/or addition of phosphate-precipitating substances.

Upon employment of nourseothricin-forming Streptomyceten stock with higher capacity for the treatment of complex phosphate-containing substrate, the sufficient provision of which in the nutrient medium is prerequisite, the dosaging of phosphate during the fermentation can be decreased to the value of zero.

Upon use of nourseothricin-forming Streptomyceten stock with higher phosphate resistance, the addition of phosphate-precipitating substances to the nutrient medium for the main culture can be decreased to the value zero. It has been found that such Streptomyceten stock of the type Streptomyces noursei simultaneously possesses a high amylolytic activity. This realization shows that physiologically different Streptomyceten stock are employed for the production techniques. Accordingly, no particularly specific Streptomyceten stock is a characteristic feature of the present invention.

With regard to the recovery of the active substance from the culture solution, it has surprisingly been found that nourseothricine can be isolated in the form of a mycelium-containing adsorbate. For this purpose, after discontinuance of the formation, the culture solution is adjusted to a weakly acid reaction, particularly pH 6.0 to 6.2, by means of addition of dilute sulfuric acid. Subsequently, a weakly acid, aqueous suspension and a physiologically non-hazardous adsorbent, for example natrified Bentonite, is well stirred into the acidified culture solution. Herewith one must observe that the acidity of the reaction solution is held within the range from pH 5.5 up to 6.5. The deposited nourseothricin-containing solid is separated by means of filtration or centrifugation, and then dried in a hot air stream to a product temperature of at most 70° C. The so produced mycelium-containing adsorbate contains 1-10%, predominantly 4-7%, active substance, calculated as nourseothricin base.

It has, moreover, been surprisingly determined that certain nourseothricin salts are only difficultly soluble in 90-95% aqueous methanol, and can be isolated and purified under the following described process conditions. For this purpose adsorbate of the nourseothricine of weakly acid cation exchangers is eluted with such dilute polybasic acids that form with nourseothricin base, methanol-insoluble salts. Subsequently, the inorganic polyvalent cations present in the eluate as accompanying material are precipitated as a salt which is weakly soluble in water. Thereafter the univalent inorganic cations are removed by means of treatment of the eluate with a highly cross-linked cation exchanger of sulfonic acid type in the H-form, and the nascent acids are neutralized with an anion exchanger in the OH-form. After the concentration of the eluate in the vacuum and removal of the impurities by means of absorption on activated carbon, there follows finally the recovery of the pure salt of nourseothricin by means of methanol-precipitation or gentle drying.

Nourseothricin sulfate is an amorphous, white powder, usually soluble in water, and difficultly soluble in methanol and most organic solvents. The elementary composition (C=32.46, 32.31; H=6.65, 6.32; N=15.73, 16.00; S=7.74, 7.60) corresponds extensively to the chemical composition of a 1:1 mixture of Streptothricine D-$(C_{31}H_{58}N_{12}O_{10} \cdot 2.5H_2SO_4 \cdot H_2O)$ and Streptothricine F-sulfate $(C_{19}H_{34}N_8O_8 \cdot 1.5H_2SO_4 \cdot H_2O)$.

Nourseothricin-oxalate is an amorphous, white powder, easily soluble in water, difficultly soluble in alcohols and other organic solvents. The elementary composition (40.31, 40.44; H, 6.24, 6.21; N 16.21, 16.49) as well as the oxalic acid content (20.12, 20.28) corresponds somewhat to the composition of a 1:1-mixture of streptothricine D-$(C_{31}H_{58}N_{12}O_{10} \cdot 2.5C_2H_2O_4 \cdot 1\text{-}3H_2O)$ and Streptothricine F-oxalate $(C_{19}H_{34}N_8O_8 \cdot 1.5C_2H_2O_4 \cdot 1\text{-}3H_2O)$.

Nourseothricin-phosphate is an amorphous white substance, easily soluble in water and difficultly soluble in alcohols and other organic solvents. The elementary composition (31.59, 31.85; H 6.25, 6.63; N 14.95, 15.18; P 10.08, 10.36) corresponds to the following composition of a 1:1 mixture of Streptothricine-D-$(C_{31}H_{58}N_{12}O_{10} \cdot 4H_3PO_4 \cdot 0\text{-}1H_2O)$ and Streptothricine F-phosphate $(C_{19}H_{34}N_8O_8 \cdot 2H_3PO_4 \cdot 0\text{-}1H_2O)$.

The novel features which are considered characteristic of the invention are set forth in particular in the appended claims. The invention itself, however, both as to its construction and its method of use, together with additional objects and advantages thereof, will be best understood from the following description of preferred embodiments.

DESCRIPTION OF THE PREFERRED EMBODIMENTS

Figure 1:
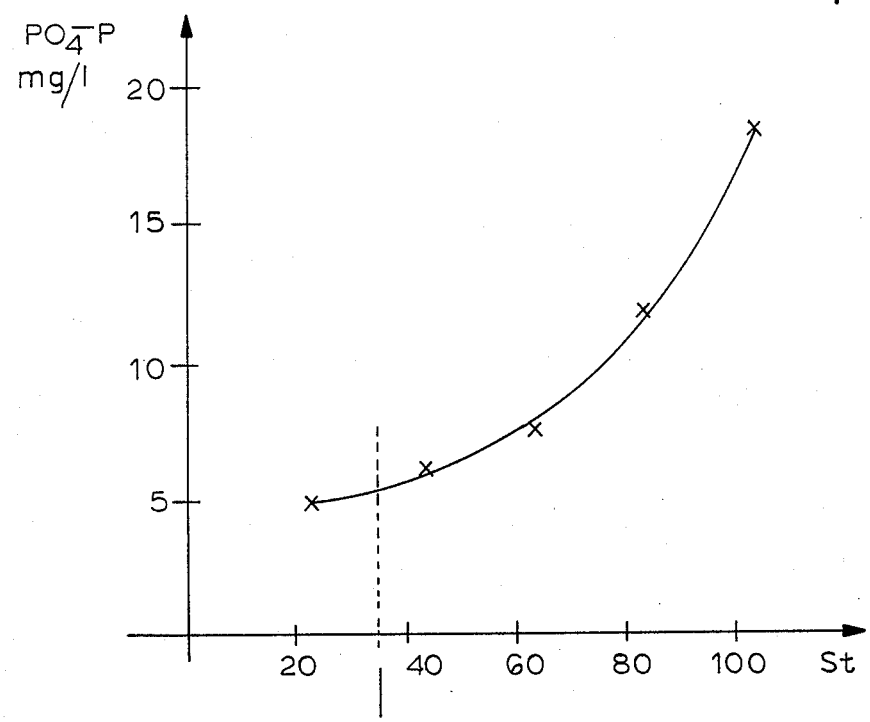

The relative antimicrobial activity of the so obtained salts can be determined microbiologically with the aid of the orifice plate diffusion test, using Bacillus subtilis ATCC 6633 as test organism. As standard, a purified nourseothricin-sulfate is used, which corresponds in its composition to a 1:1-mixture of Streptothricine D-$(C_{31}H_{58}N_{12}O_{10} \cdot 2.5H_2SO_4 \cdot H_2O)$ and Streptothricine F-sulfate $(C_{19}H_{34}N_8O_8 \cdot 1.5H_2O)$ and contains 702 µg base/mg. The conditions for the microbiological value determination are to be so chosen that 0.05 ml of a test solution containing 10 µg nourseothricin base per ml provides with a signal hole diameter of 9 mm an inhibition zone of 19±1 mm diameter.

EXAMPLE 1

A conserve of spores of the stock Streptomyces noursei ZIMET 43716, dried lyophilically on earth, is scattered onto a suitable agar medium, for example Emerson agar. After about 7 days incubation at 30° C., approximately 2 cm² size pieces of the mycelium grass are cut out, and a culture start of the first pre-culture is inoculated therewith.

The medium of this pre-culture has the following composition per liter: 40.0 g glucose; 15.0 g soy extraction groats; 0.3 g $KH_2PO_4$; 5.0 g NaCl; 3.0 g $CaCO_3$; tap water to 1000 ml; pH 6.5 to 6.9 (before sterilization).

This medium is run off, in amounts of always 50 ml, into 500 ml closed vertical throat flasks, closed with wadding cork. The sterilization follows by means of 35 minutes duration of heating to 121° C. in autoclaves.

The inoculated charge is incubated 48 hours as a so-called agitated culture at 29° C. The culture charge of the main culture is inoculated with always 3 ml of the so-obtained pre-culture.

For the main culture, per liter tap water, the following basic media are employed:
  Medium Bo-30 29.0 g glucose; 13.0 soy extraction groats; 5.0 g NaCl; 3.0 g $CaCO_3$; tap water to 1000; pH 6.5 (before sterilization)
  Medium Bo-31 30.0 g cornstarch; 3.0 g glucose; 7.0 g soy extraction groats; 5.0 g $NH_4NO_3$; 2.0 g $MgSO_4$; 5.0 g NaCl; 3.0 g $CaCO_3$; tap water to 1000; pH 6.0 (before sterilization).

The nutrient media of the main cultures are drawn off in amounts of 80 ml each into 500 ml vertical throat flasks, closed with wadding cork, and are sterilized for 30 minutes at 121° C. in autoclaves.

Corresponding to the test plan, the so treated charges to the main culture at the time point of inoculation are used with sterile filtrated, aqueous, neutral solutions of the concerned substances set forth in Tables 1 and 2 (maximal 3.0 ml addition/80 ml medium).

The maximal nourseothricin concentrations determined during the 72-120 hours incubation of the main culture are in so-called agitating plates (180 rpm) at 26° C. with the aid of orifice plate diffusion test using Bacillus subtilis ATCC 6633 as test bacillus, are set forth in Tables 1 and 2. The further working-up follows according to Examples 8-13.

EXAMPLE 2

A batch of spores of the variety NG 13-14 of nourseothricin-forming stock ZIMET 43716, dried lyophillically on earth, is scattered onto a suitable agar medium, for example Emerson agar. After about 7 days incubation at 30° C., approximately 2 cm² size pieces of the mycelium grass are cut out, and a culture start of the pre-cultivation is inocculated therewith. The cultivation medium contains per liter tap water the following components: 40 g glucose; 15 g soy extraction groats; 0.3 g $KH_2PO_4$; 5 g NaCl and 3 g $CaCO_3$. The acidity is adjusted before the sterilization to the value pH 6.5. This medium is filled, in amounts of 50 ml, into 500 ml vertical throat flasks, closed with wadding cork. The sterilization follows by means of 35 minutes heating to 121° C. in autoclaves.

The inocculated pre-cultivation charge is incubated 48 hours as a so-called agitation culture at 29° C. The 2,500 ml containing culture charge of the main culture in the laboratory fermenter is inocculated with 150 ml of the so-obtained pre-cultivation.

The medium Bo-34 is used for the main culture, which per liter of tap water contains the following components: 32 g potato starch; 29 g glucose; 11 g soy extraction groats; 11 g $(NH_4)_2SO_4$; 2 g $MgSO_4\cdot 7H_2O$; 1 g NaCl; 6 g $CaCO_3$ and 0.5 g $ZnSO_4\cdot 7H_2O$. 1 ml Antaphron is added to 2500 ml nutrient medium, as a defoamer of silicon basis. Before the sterilization the acidity has the value pH 6.0. After the sterilization of the fermenter culture vessel filled with 2500 ml, at 121° C. in autoclaves, and recooling to 30° C., the starting acidity is adjusted to the value pH 6.8 by means of aseptic addition of 10% sterile sulfuric acid. The inocculated fermentation charge is incubated 168 hours at a temperature of 30° C. and an aeration rate of 2500 ml air per minute, under stirring of 800 rotations per minute. At 1.5 hours after inoculation of the main culture a solution of 4 g $KH_2PO_4$ per liter distilled water is continuously dosed in over a time period of 5 hours at a rate of 1.8 ml/hour by means of a peristaltic pump; subsequently this addition follows over a time period of 21 hours with a dosing rate of 3.5 ml/hour. During the fermentation, periodic samples of the culture solution are withdrawn under aseptic conditions, and their content of nourseothricin base is determined by means of the orifice plate diffusion test using Bacillus subtilis ATCC 6633 as test bacillus, in glucose, in ammonium nitrogen and in solids. The parameters $pO_2$, pH and $CO_2$-content in the exhaust air are followed during the course of the process by means of registering measurement. The drop in the acidity of the culture solution below the value pH 5.8 is prevented by means of dosaging of sterile 5% caustic soda.

Upon lowering of the glucose concentration to 5 g/l, or the ammonium nitrogen to 0.5 g/l, recognizable in an increase of the pH-value and the $pO_2$-value as well as the lowering of the $CO_2$-content in the exhaust air, 25 g glucose or 10 g $(NH_4)SO_4$ are discontinuously added as concentrated, sterile solution.

A further fermentation is performed under otherwise similar conditions, however without dosaging of $KH_2PO_4$, glucose and $(NH_4)_2SO_4$. Upon completion of the fermentation the culture solution displays still clearly detectable amounts of free glucose and free ammonium. The determined concentrations of nourseothricin base in the culture filtrate from both different fermentations are set forth in Table 3.

EXAMPLE 3

A batch of mycelium (growth weight of about 300 mg) of the nourseothricin-forming Streptomyceten-stock mentioned in Example 2, lyophillically dried on glucose-gelatin, is deposited with 3 ml of a 0.9% NaCl solution. 0.5 ml of this suspension serves as inocculum for 400 ml cultivation of the first stage.

The pre-cultivation medium has the same composition and acidity as that given in Example 2. This medium is filled, in amounts of 400 ml each, into 2500 ml vertical throat flasks, closed with wadding cork. The sterilization follows by means of 35 minutes heating to 121° C. in autoclaves.

The charge, recooled to room temperature and inocculated, is incubated 48 hours as a so-called agitation culture (180 rpm) at 29° C. As a second stage of the pre-cultivation, a fine steel fermenter (250 ml growth volume) with arrangements for sterile aeration and a stirrer, and filled with 150 l of heat-sterilized medium (60 minutes at 121° C.) of the same composition as in the first pre-culture stage, is inocculated with 1200 ml of the so-obtained culture solution of the first pre-cultivation. The cultivation follows at 27°-29° C., with a stirrer velocity of 240 rpm and an aeration rate of 1 liter air per leter culture solution per minute.

Serving for the main culture is a fine steel fermenter (710 liter gross volume), provided with arrangements for sterile aeration and a centrally placed stirrer, which is filled with 500 liter nutrient medium Bo-34 (recipe, see Example 2). As de-foamer, 0.5 g/l Antaphron is added. The acidity is adjusted before the sterilization to the pH-range of 6.7 to 7.0. The sterilization of the nutrient medium (without glucose portion) follows in situ through pre-heating with jacket vapor to about 70° C., and subsequent heating by means of direct vapor to 121° C. for 15 minutes. After the cooling to about 30° C., the sterilized glucose, separated in the form of a 50% aqueous solution through 30 minutes heating to 121° C., is added under aseptic conditions. Before the inoculation the adjustment of the starting acidity takes place to a value between pH 6.9 and 7.1 by means of sterile 10% sulfuric acid.

The fermenter charge of the main culture, always inocculated with 5% inocculum from the second pre-cultivation stage, is cultivated 120 hours at temperatures between 28° and 30° C., an aeration rate of 500 liter air per minute (pressure 0.14 to 0.16 MPa) under stirring (320 rpm).

At the second hour after the inoculation, 87 g $KH_2PO_4$ as aqueous solution is dosed to one of both fermenter charges by means of peristaltic pumps, and at a constant rate. Upon dropping of the acidity to below pH 6.3, the readjustment of this pH-value is undertaken by means of sterile 25% aqueous ammonium hydroxide solution.

During the fermentation and under aseptic conditions, periodically samples of the culture solution are withdrawn. The concentrations of nourseothricin base are determined in the samples by means of the orifice plate diffusion test using Bacillus subtilis ATCC 6633 as test bacillus, in glucose, in ammonium nitrogen and in solids. The parameters pH and $CO_2$-content in the exhaust air are followed throughout the course of the process by means of registering measurements.

Upon dropping of the glucose concentration below 5 g/l, or the ammonium nitrogen below 0.5 g/l, recognizable by an increase in the measured pH-value and a lowering of the $CO_2$-content in the exhaust gas, 5000 g glucose or 1800 g ammonium sulfate are added as concentrated, sterile aqueous solutions, discontinuously.

The other fermenter charge receives no dosaging of phosphates, glucose or ammonium sulfate. A pH-regulation does not take place; the continuously measured acidity values move within the range of pH 6.4 and pH 7.2. Upon termination of the fermentation the culture still contains amounts above 5 g/l of glucose and 0.5 g/l ammonium nitrogen.

The concentrations of nourseothricin base determined in the culture filtrate of both different fermentations are set forth in Table 4.

EXAMPLE 4

The suspension of a mycellium lyophil batch in physiological saline solution of a production stock of Streptomyces noursei serves as inocculum for the first submersed passage. The nutrient medium contains per liter of tap water: 15 g glucose; 15 g soy extraction groats; 0.3 g $KH_2PO_4$; 5.0 g NaCl; 1.0 g $CaCO_3$; pH 6.5 to 6.9 (filled in 50 ml amounts into 500 ml agitation vessels).

The sterilization of the medium follows at 120° C. for 35 minutes. After 48 hours cultivation at 28° C. on a rotation agitation machine the second submersed passage (filling of 250 ml, 2000 ml agitation vessel) is cultivated in a ratio of 1 part inocculum to 25 parts nutrient medium, over 24 hours on the rotation agitation machine.

600 ml of the second submersed passage are used for the inocculation of 800 l inocculated fermenter medium. The nutrient medium contains per liter: 15 g glucose; 15 g soy extraction groats; 0.3 g $KH_2PO_4$; 5.0 g NaCl; 1.0 g $CaCO_3$; 5 g Antaphron; 37.5 g sunflower oil.

The pH-value is adjusted before the sterilization to 7.2-7.4, and amounts to from 6.8 to 7.0 after the finish of the sterilization. The sterilization takes place at 120° C. for 60 minutes. After about 30 hours cultivation at 28° C., about 60 mg/l soluble phosphate has been consumed, and therewith 12-15 g/l biomass formed. The inocculum amount of 800 l is sufficient for the inocculation of about 18 $m^3$ of product formation medium of the main culture. The nutrient medium of the production fermenter contains per liter: 32.0 g potato starch; soy extraction groats 15.0 g; 1.0 g NaCl; 6.0 g $CaCO_3$; 0.5 g $ZnSO_4 \cdot 7H_2O$; 2.0 $MgSO_4 \cdot 7H_2O$; 3.0 g sunflower oil; 0.3 g Antaphron; 29.0 g glucose; 6.0 g $(NH_4)_2SO_4$. The components glucose and ammonium sulfate, after separate sterilization (120° C., 30 minutes) introduced to the nutrient medium.

Sterilization of the medium follows at 115° C. for 60 minutes, whereby before the start a pH-value from 7.5 to 7.8 is adjusted, and after completion of the sterilization a value between 7.2 and 8.2 is obtained.

The completed medium attains a pH-value between 7.0 and 7.4. The fermentation follows at 28° C. with an aeration ratio of 0.3 VVM (volumes air per volume culture solution per minute) at 0.02 MPa and an oxygen partial pressure of 60%.

When the values for glucose and ammonium nitrogen drop below the respective limit values of 15 g/l and 0.2 g/l, these components are dosed in as 50% sterile solutions, until the culture solution attains a pH-value of 5.2 with an ammonium nitrogen value above 300 mg/l.

The further addition of ammonium nitrogen follows by means of the dosaging of ammonia water with constant pH-value of 5.5. After a fermentation period of 130 hours, a biological activity of 8000 to 11000 μg nourseothricine/ml culture solution is formed.

EXAMPLE 5

For inoculation material cultivation, 2.5 l vertical throat flasks, which each contain 400 ml sterilized nutrient medium, containing per liter: 40 g glucose; 15 g soy extraction groats; 0.3 g $KH_2PO_4$; 5 g NaCl; 3 g $CaCO_3$; and tap water to 1000 ml, are inoculated with 0.5 ml of a mycelium batch deposit of a variety of Streptomyces nourcei ZIMET 43716. The cultivation follows at 29° C. over 48 hours on a ground, oscillating vibration table. Serving as the second pre-cultivation stage are fine steel fermenters (gross volume 240 l) filled with 180 l vapor sterilized medium (45 minutes at 120° C.) of the same composition as in the first pre-cultivation stage, which are inoculated each with 800 ml of the culture solution from the first pre-cultivation stage. The cultivation follows over 40 hours at 28°-29° C., a stirrer rotation speed of 240 rpm and an aeration rate of 1.0 VVM.

For the main culture are employed fine steel fermenters (gross volume 4200 l) which are filled with 2500 l nutrient solution of the following basic composition: 62.5 g cornstarch; 2.5 g glucose; 16 g soy extraction groats; 11 g $NH_4SO_4$; 2 g $MgSO_4 \cdot 7H_2O$; 1 g NaCl; 6 g $CaCO_3$; 0.5 g polypropylene glycol; tap water to 1000. To this basic charges are added in one case per liter tap water 0.5 g $ZnSO_4 \cdot 7H_2O$, in the other case 0.1 g $Fe_2(SO_4)_3 \cdot 7H_2O$. The acidity of the nutrient solution is adjusted before the sterilization to the pH-value 6.2. The sterilization (without glucose portion) follows through heating by means of direct vapor to 120° C. for 15 minutes. After cooling to 29° C., the glucose, sterilized and separated in the form of a 50% aqueous solution, is aseptically added. Before the inoculation follows an adjustment of the starting acidity of the nutrient solution by means of sulfuric acid to the pH-value 6.8±0.1.

The fermentation charges are inoculated with 4% inoculum from the second pre-cultivation stage. The cultivation follows over 140 hours at 29° C., an aeration rate of 0.5 VVM (0-20 hours) where 1.0 VVM ($20^{th}$ to $140^{th}$ hours) at 0.03 MPa excess pressure under stirring at 180 rpm. The acidity of the culture solution is constantly regulated after its lowering to a pH-value of 6.0±0.1 by means of 25% ammonium hydroxide solution.

In the biological test, the following nourceothricin concentrations were determined in the culture solutions:

| Fermentation hour (h) | Nourseothricin Concentration (μg/ml) | |
| --- | --- | --- |
| | $ZnSO_4 \cdot 7H_2O$ | $Fe_2(SO_4)_3$ |
| $92^{th}$ | 4900 | 5100 |
| $116^{th}$ | 7100 | 6800 |

-continued

| Fermentation hour (h) | Nourseothricin Concentration ($\mu$g/ml) | |
|---|---|---|
| | ZnSO$_4$.7H$_2$O | Fe$_2$(SO$_4$)$_3$ |
| 140$^{th}$ | 8300 | 8000 |

EXAMPLE 6

For inocculation material charges, in the first stage, 2.5 l vertical throat flasks, which each contain 400 ml sterilized nutrient medium (15 g peanut extraction groats; 10 g corn spring water (100% dry substance); 40 g maltose; 5 g (NH$_4$)$_2$SO$_4$; 6 g CaCO$_3$; tap water to 1000), are inoculated each with 0.5 ml of a mycelium batch deposit of a variety of Streptomyces noursei ZIMET 43716. The cultivation follows at 29° C. over 48 hours on a round vibrating agitation table.

Serving as the second pre-cultivation stage are fine steel fermenters (gross volume 240 l) filled each with 150 l vapor sterilized medium (30 minutes at 120° C.) of the same composition as in the first pre-cultivation stage, inoculated each with 800 ml of the culture solution obtained from the first pre-cultivation stage. The cultivation follows over 40 hours at 28°–29° C., a stirrer rotation speed of 240 rpm and an aeration rate of 1.0 VVM with an excess pressure of 0.03 MPa.

For the main culture a fine steel fermenter (gross volume 720 l) is used, which is filled with 500 ml nutrient solution of the following composition per liter: 60 g cornstarch; 25 g peanut extraction groats; 10 g corn spring water (100% dry substance); 10 g (NH$_4$)$_2$SO$_4$; 5 g calcium carbonate; 3 g sunflower oil; tap water to 1000. The pH-value of the nutrient solution is adjusted before the sterilization to pH 6.8–7.0. The sterilization follows over 30 minutes at 120° C.

The fermentation charge is inoculated with 5% inocculation material from the second pre-cultivation stage. In the course of the fermentation, additionally 30 g cornstarch per 1 culture are added twice, as 30% suspension (after liquefaction of the aqueous deposit in known manner through treatment with enzyme preparations with amylolytic activity, for example brewery enzymes and subsequent sterilization). The acidity of the culture solution is held constant to a pH-value of 6.2±0.1 by means of 25% ammonium hydroxide solution.

After the course of a 144 hour fermentation at 29° C., a stirrer velocity of 320 rpm and an aeration rate of 0.75 VVM with an excess pressure of 0.03 MPa, 580 l culture solution are obtained, in which a production concentration of 6850 $\mu$g nourseothricine per ml is determined.

EXAMPLE 7

Figure 2:
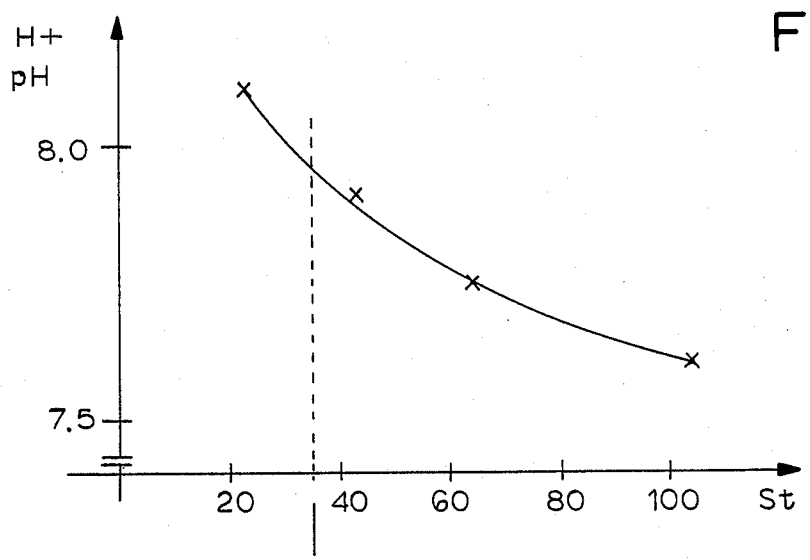

Serving for the main culture is a fine steel fermenter (4200 liters gross volume) provided with arrangements for sterile aeration and a centrally placed stirrer, which is filled with 2500 liters nutrient medium of the following composition per 1 liter tap water: 32 g potato starch; 60 g glucose; 11 g soy extraction groats; 11 g (NH$_4$)$_2$SO$_4$; 2 g MgSO$_4$.7H$_2$O; 1 g NaCl, 6 g CaCO$_3$; and 0.5 g ZnSO$_4$. 0.5 g Antaphron NM 40 are added as de-foamer, per liter culture solution. The acidity is adjusted before the sterilization to the pH-value 6.2. The thermal, in situ sterilization of the nutrient medium (without glucose portion) followed with direct vapor base upon the sterilization functional value as a standard. The nominal value for this regulation lies at St=35 (contamination risk with 10$^{-3}$, cell density 5·10$^6$ cells/ml culture solution before the sterilization) and is maintained with a plateau temperature about 120° C. through control of the amount of the introduced direct vapor. The actual value of the sterilization functional St is determined according to $$St = \int_0^t f[A, E, T(\tau)] d\tau$$

with f as Arrhenius function from the actual course of the sterilization temperature T(t). The FIGS. 1 and 2 show the dependence of the concentration of the acid-soluble phosphate in the recooled sterilized nutrient medium and its acidity on the nominal value of the sterilization functional, St±35 corresponding to the adjustment of the starting concentration of the available phosphate to 5 mg/l pH 8.0.

The lowering to the physiologically necessary pH-value of 7.4 at the start of fermentation is realized by means of the addition of sulfuric acid, which thereafter is aseptically added in the form of a 50% aqueous solution of separately sterilized glucose portion (30 minutes to 120° C.). The fermentation charge of the main culture, inoculated with 4% inoculum from the second pre-cultivation stage, is cultivated for 120 hours at 29° C., an aeration rate of 1250 liters per minute (0$^{th}$ to 12$^{th}$ hour) or 2500 liters per minute (12$^{th}$ to 120$^{th}$ hour) at 0.03 Pa excess pressure, under stirring of 180 rpm.

Figure 3:
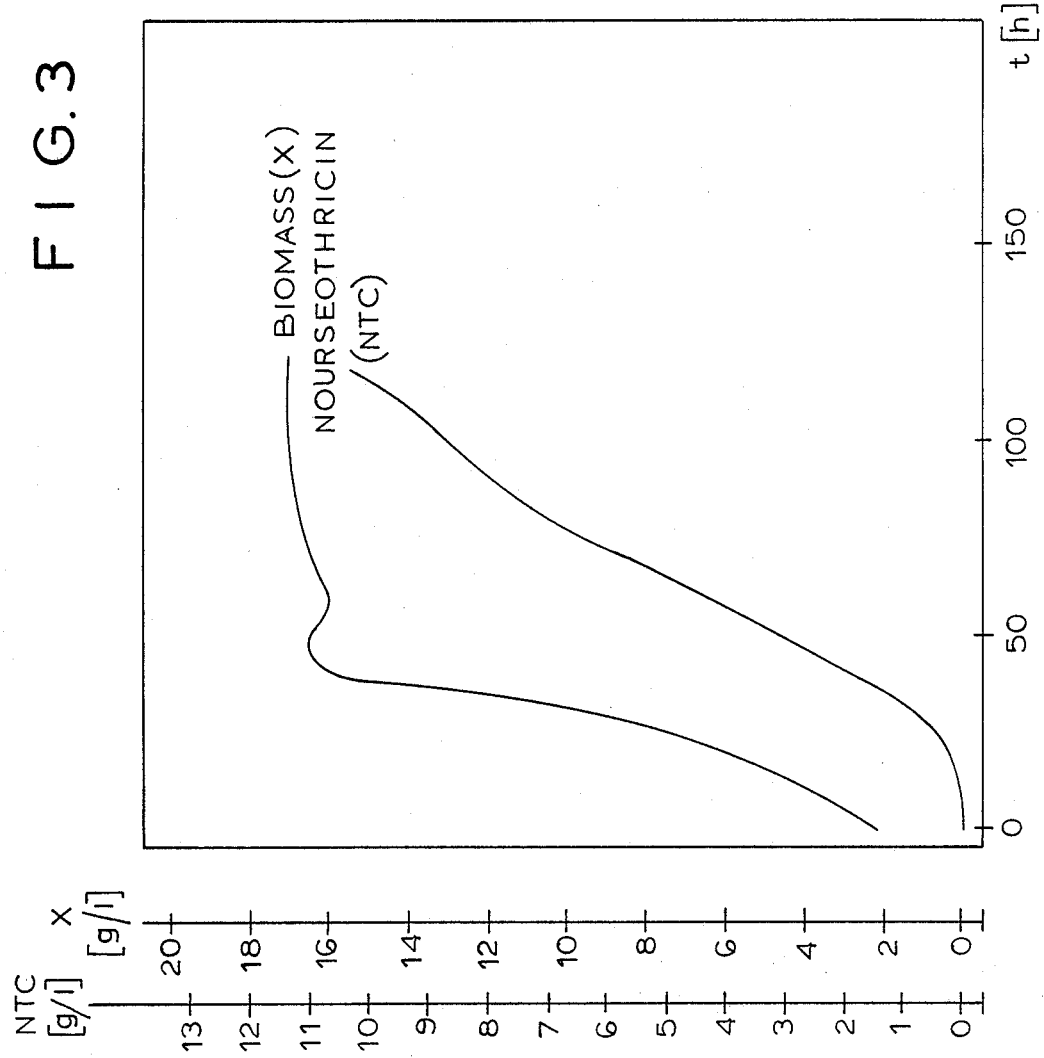

The course of the fermentation shows:

FIG. 3: time course of the produced antibiotic nourseothricine and the dry weight of the biomass.

Figure 4:
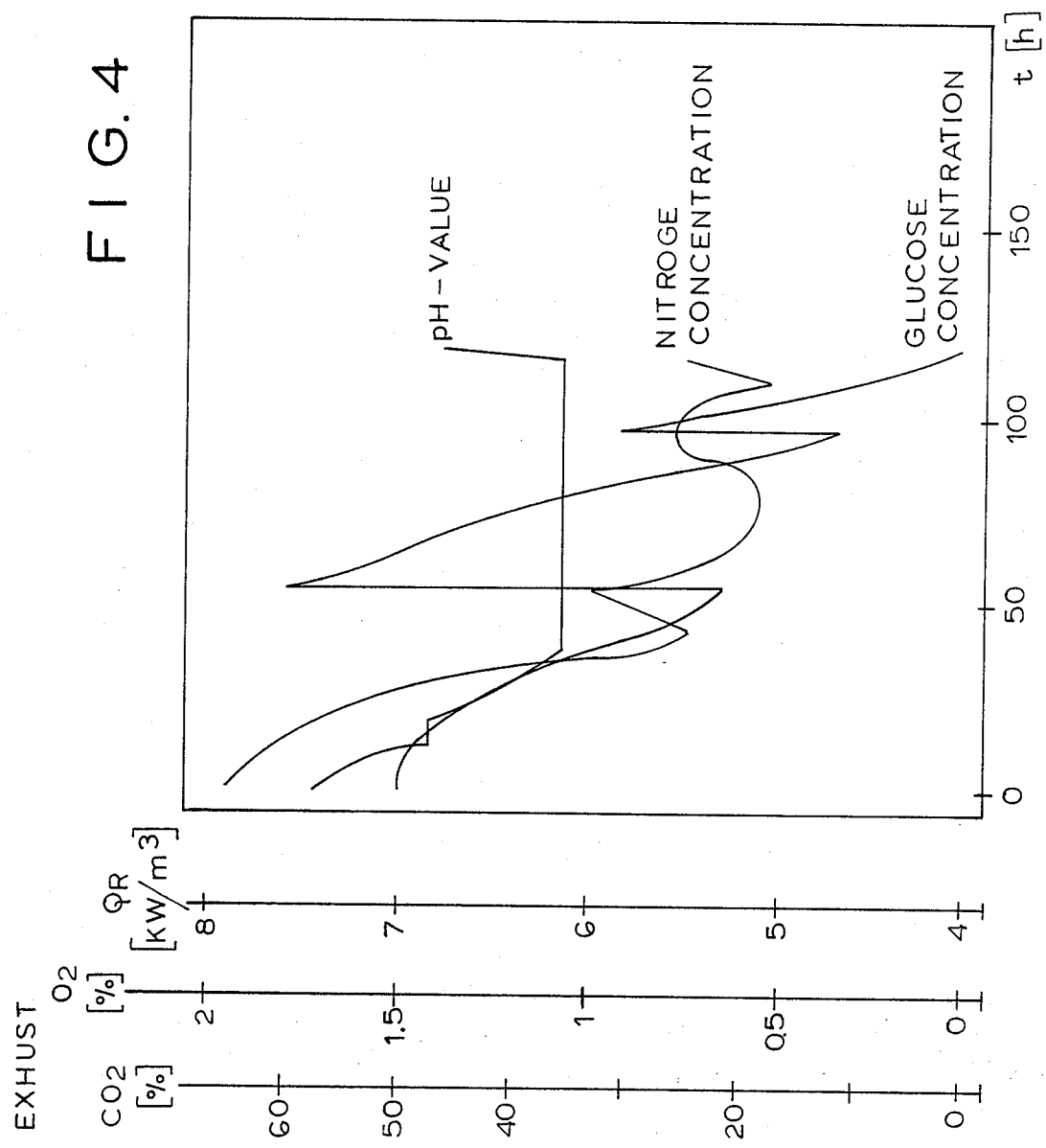

FIG. 4: time course of the pH-value, the glucose and ammonium nitrogen concentration.

Figure 5:
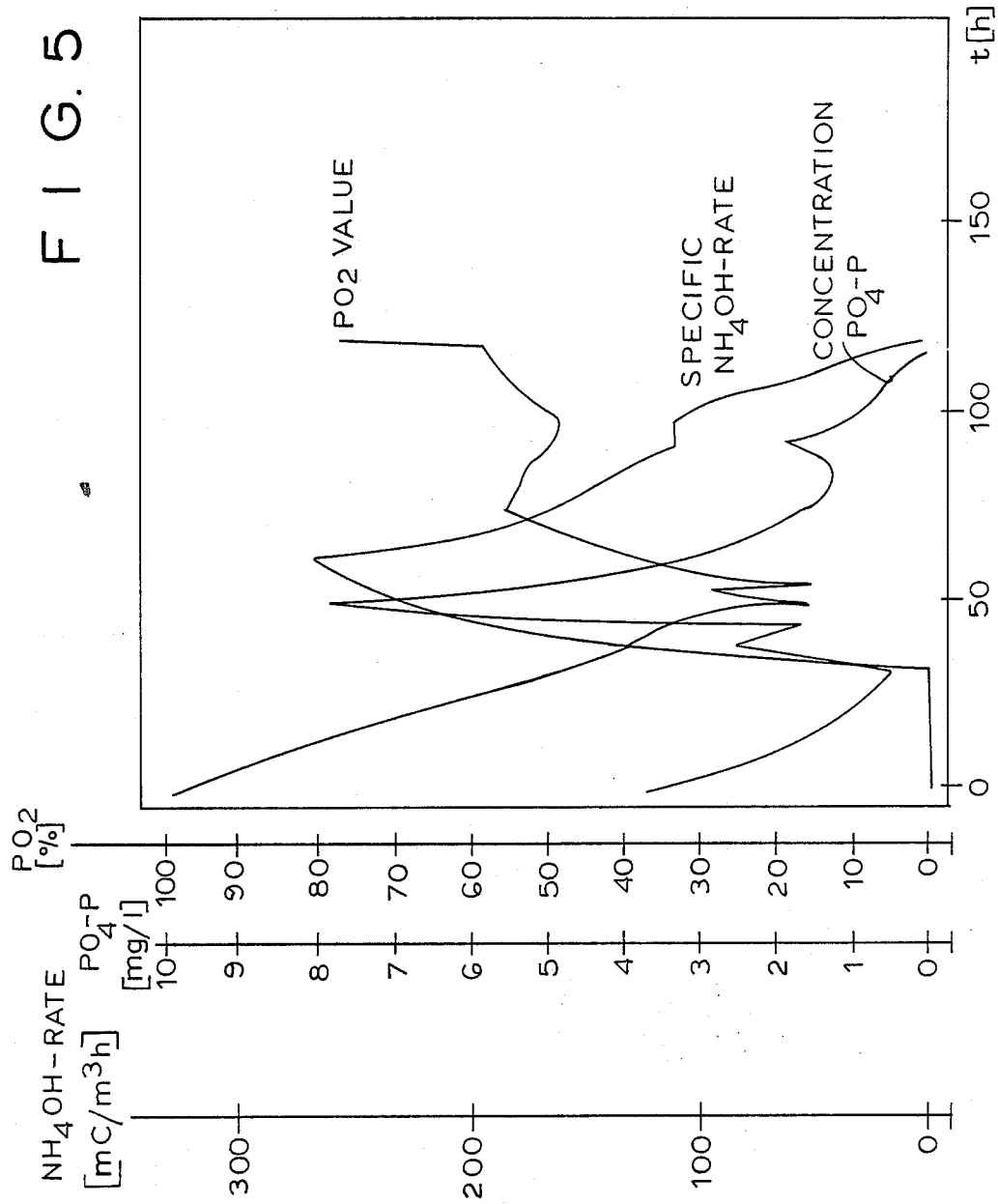

FIG. 5: time behavior of the ammonium hydroxide dosaging rate, the phosphate concentration and the dissolved oxygen concentration.

Figure 6:
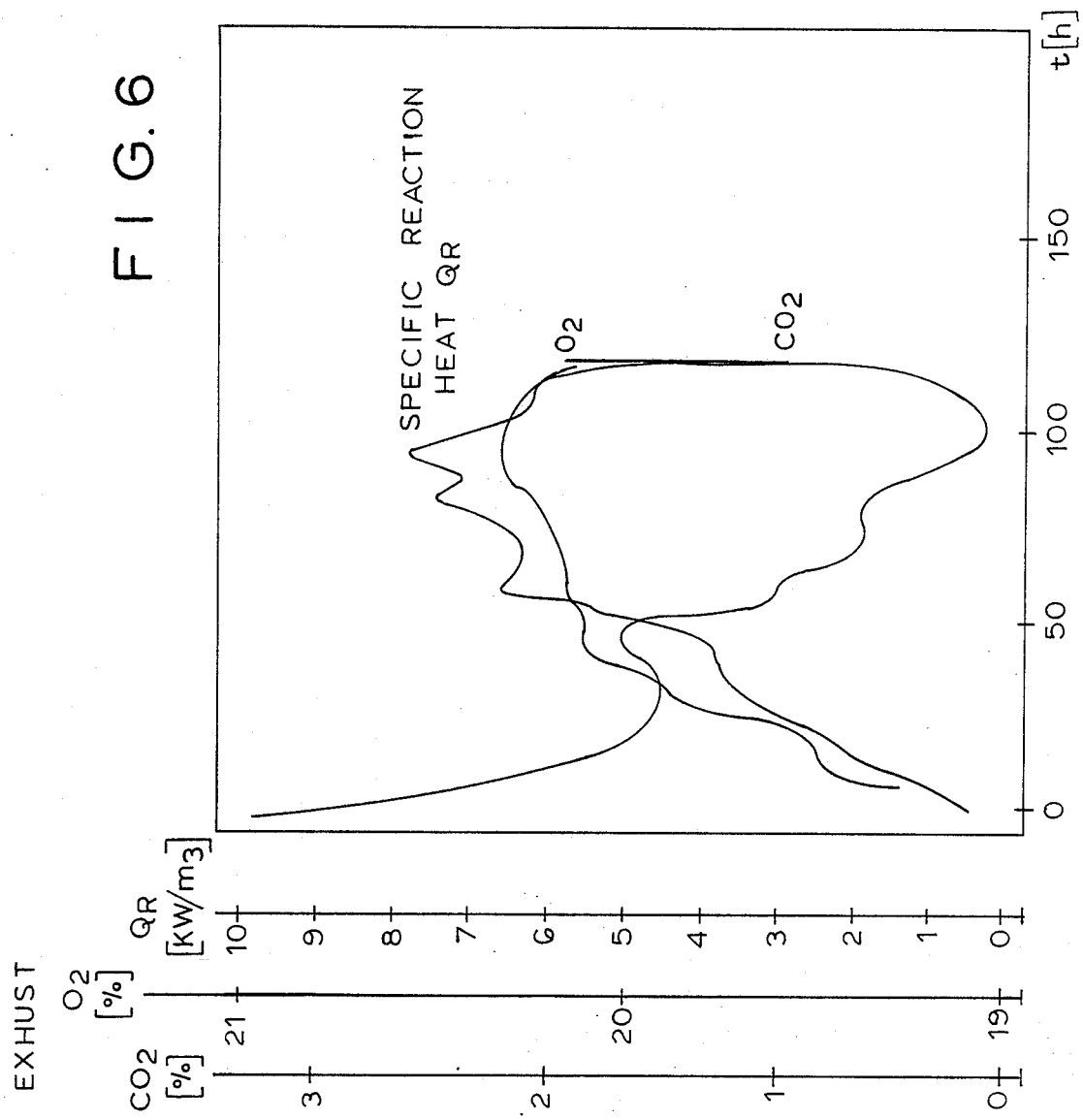

FIG. 6: time course of the exhaust gas composition of oxygen and carbon dioxide, as well as the reaction heat.

FIG. 7: time course of the specific product formation rate and the specific growth rate.

The fermentation is performed manually discontinuously with regard to the regulation parameters by means of direct phosphate dosaging and glucose dosaging after measurement of the behavior of the ammonium hydroxide dosaging rate. The pH-nominal value interval is 6.2±0.05 and the lower limit pH 6.15 is obtained after 38 hours fermentation time.

For direct phosphate dosaging, a sterile aqueous solution of KH$_2$PO$_4$ is employed. During the first 32 hours the solution is so dosaged that for stimulation of the material exchange activity a total of 42 mg phosphorus per liter culture solution is added in the form of phosphate.

Fixed by means of the chosen pH-nominal value interval, the buffering state of the nutrient medium and the caustic concentration, the ammonium hydroxide (25%) dosaging is instituted after the 38$^{th}$ hour.

The observed decrease in the rise of the ammonium hydroxide dosaging rate is realized by means of direct phosphate dosaging of always 8.5 mg phosphate-phosphorus per liter culture solution between the 47$^{th}$ and 48$^{th}$ hour or 53$^{rd}$ and 54$^{th}$ hour.

Thereby the dosaging rate attains its maximal value after the 62$^{nd}$ hour and then the passage from direct to indirect phosphate dosaging, by means of setting free from substrates, is correspondingly decreased. In this manner after about 20 hours fermentation there occurs approximately the optimal specific dosaging rate of 230 ml 25% ammonium hydroxide solution per cubic meter culture solution and hour. The added ammonium hydroxide solution is sufficient in order to hold the nitrogen concentration in the physiologically favorable range. Accordingly, no further nitrogen sources are dosed in. With regard to the carbon sources, the strengthened decrease in the rise of the ammonium hydroxide dosaging rate after the second phosphate dosaging is a cause for the dosaging of 48 g glucose per liter culture solution at the $56^{th}$ hour. The indication of the passage to indirect phosphate dosaging at about the $95^{th}$ hour is used for realization of the second glucose dosaging of 18 g glucose per liter culture solution.

With the direct phosphate dosaging, no limitation is provided with regard to the concentration of the dissolved oxygen. Reaction heat and exhaust air composition evidence the state of the fermentation phase, and serve for the avoidance of substrate limitations. The nourseothricin end value of 1050 μg/ml culture solution is attained in that the effective specific product formation rate lies over the time period of 48 hours between $8 \cdot 10^{-3}$ per hour and $9 \cdot 10^{-3}$ per hour. Moreover, the employed glucose is completely fermented and the technically dictated biomass limit is not exceeded.

EXAMPLE 8

For isolation of the antibiotic, 750 l fermentation solution with a content of 2900 μg/ml nourseothricin base is reacted with a saturated aqueous solution of 7.6 kg oxalic acid. After adjustment of a pH 4.2 with ammonia, the solution is briefly heated to 70° C., the solid portion is separated off, the culture filtrate is neutralized with ammonia, and for the removal of impurities, separated again, and then led for adsorption with a velocity of 25 l/hr through two successively placed columns with each 5 l Wofatite CP (Na-form) from the bottom upwardly. The adsorbates of both columns are successively washed with 30 l water, 20 l 0.1 N acetic acid, and 15 l water. Thereafter the antibiotics are eluted with 20 l 0.5 N sulfuric acid and subsequently with 10 l water. Eluate with pH-values below 3.0 are neutralized with Wofatite AD 41 (OH-form).

The eluate from column I (32.8 l) is reacted under stirring with diammonium hydrogen phosphate and ammonia until with pH-values from 7.5 to 7.7 no more precipitation is produced. After separation of the precipitated inorganic phosphate through filtration, the clear filtrate is filtered for de-salting with a velocity of 20 l/hr across 10 l Wofatite KP 16 (H-form) and subsequently across 10 l Wofatite AD 41 (OH-form). After washing of the exchange resin with 20 l water, eluate and wash water are combined (about 55 l), concentrated in a vacuum at 30°-40° C. to 6.5 l, and treated with 100 g activated carbon. The filtrate is adjusted to a pH-value of 4.0-4.5 with sulfuric acid, and subsequently, with stirring, dropped into 75 l methanol, whereby amorphous nourseothricin sulfate is precipitated. The sediment is filtered off, washed with methanol and dried in a vacuum at 40° C.

The eluate from column II is treated in similar manner.

Yield:
Column I: 745 g nourseothricin-sulfate; $[\alpha]_D^{25} = -27.5°$ (c=1; water); sulfate ash; 2.2% microbiological activity: 687 μg/mg;

Column II: 579 g nourseothricin-sulfate; sulfate ash: 2.0% microbiological activity: 470 μg/mg.

EXAMPLE 9

9.6 l of an eluate fraction obtained and de-salted according to Example 8 are evaporated in a vacuum at 30°-40° C. to a volume of 440 ml. The eluate concentrate is treated with 12 g activated charcoal and after filtration, adjusted to pH 6.0 with sulfuric acid.

Spray Drying 220 ml of the de-colored eluate concentrate (solids content 33%) are spray dried in a laboratory spray drier Büchi Mini Spray Dryer 190 with an air entry temperature of 165°-175° C. and an exit temperature of 85°-90° C.

Yield: 58.4 g nourseothricin-sulfate microbiological activity 980 μg/mg $[\alpha]_D^{25} = -32.8°$ (c=1.29; water); sulfate ash 0.4%; water content: 6.0%; C 36.87, 37.01; H 6.48, 6.66; N 16.99, 16.95; S 5.64, 5.71.

Freeze-drying 220 ml of the de-colored eluate concentrate are dried at a product exit temperature of −20° C. and a final pressure of 0.03 Torr in a freeze drying plant TG 5 (manufacturer: VEB Hochvakuum Dresden).

Yield: 71.5 g nourseothricin-sulfate microbiological activity: 994 μg/mg $[\alpha]_D^{23} = -34.2°$ (c=1.28; water) water content: 3.0%; C 36.85, 36.98; H 6.32, 6.32; N 16.89, 17.16; S 5.87, 5.85.

The elementary analysis corresponds approximately to the following composition of a 2:1 mixture of Streptothricine D-and Streptothricine F-sulfate: $2C_{31}H_{58}N_{12}O_{10} \cdot 2H_2SO_4 \cdot 2H_2O + C_{19}H_{34}N_8O_8 \cdot H_2SO_4 \cdot 2H_2O$).

EXAMPLE 10

For adsorption of the antibiotic, 75 l of a culture filtrate obtained according to Example 8, with 4846 μg/ml nourseothricin base, are led rising, with a velocity of 4 l/hr through a column with 2 l Wofatite CP (Na-form). The resin is subsequently washed in turn with 15 l aqua dest., 9 l 0.1 N acetic acid and 10 l aqua dest., and thereafter the antibiotic is eluted with 14 l 0.5 N phosphoric acid. The eluate (pH 3-4) is neutralized through stirring with 2 l Wofatite AD 41 (OH-form). Precipitated calcium phosphate is filtered off together with the ion exchanger, and the filtrate is reacted with ammonia to a pH 7.7, whereby ammonium magnesium phosphate is precipitated and removed by means of filtration. Subsequently, univalent cations are separated from the nourseothricin phosphate solution through stirring in with 1 l Wofatite KP 16 (H-form). Thereafter the solution (17 l) is evaporated in a vacuum at 40° C. to 1.5 l, acidified with phosphoric acid to a pH 4.5, and then treated with 7.5 g activated carbon. The clear filtrate is dripped into 20 l methanol. Nourseothricin phosphate remaining colloidally in solution is brought to coagulation and into a well filterable form by means of the addition of 25% dimethylamine solution. The sediment is filtered off, washed with methanol and dried in a vacuum across calcium chloride.

Yield: 169.5 g nourseothricin-phosphate; $[\alpha]_D^{25} = -29.9°$ (c=1; water); sulfate ash 1.06% microbiological activity: 818 μg/mg.

EXAMPLE 11

75 l of a culture filtrate obtained according to Example 8, with 3000 μg/ml nourseothricin base, are led rising with a velocity of 4 l/hr through a column with 2 l Wofatite CP (Na-form). After washing the resin with 15 l aqua dest., 10 l 0.1 N acetic acid and once again 10 l aqua dest., the antibiotic is eluted with 10 l 0.5 N oxalic acid. The eluate (11 liters) is neutralized by means of stirring with 2 l Wofatite AD 41 (OH-form), precipitated salts and ion exchanger are filtered off together, and the clear filtrate is stirred with 2 l Wofatite KP 16 (H-form) for removal of univalent cations. Subsequently, the solution is neutralized with 0.5 l Wofatite AD 41 (OH-form) and evaporated in a vacuum at 40° C. to 800 ml. The concentrate is treated with 7 g activated carbon and, after filtration, dripped into 12 l methanol. Nourseothricin-oxalate remaining colloidally in solution is coagulated by means of addition of 25% dimethylamine solution, and brought to a well filterable form. The filtered off sediment is washed with methanol and dried in a vacuum across calcium chloride.

Yield: 162 g nourseothricin-oxalate $[\alpha]_D^{25} = -41.8°$ (c=1; water); sulfate ash: 0.9% microbiological activity: 809 μg/mg

EXAMPLES 12 AND 13

In swine mast tests, by means of delivery of a mixed feed agent (premix) supplemented with 40 mg/kg dry substance (DS) nourseothricin-hydrochloride during the 70 test days, a 6% improved average living mass development is determined. By provision of 21 mg/kg dry substance nourseothricin as mycelium adsorbate with the feed rations, during the 70 days mast test the average daily living mass addition is raied about 23%, whereby the feed expenditure is 7% less than it was with the animals of the control group.

The provision of nourseothricin in the form of mycelium adsorbate in staggered dosages up to 52.5 mg active substance/animal/day to calves exerts a very favorable influence on the animal health, recognized by a clear drop in the number of deaths and a drastic lowering of the illness days. The most favorable activity with regard to the living mass addition of calves were determined particularly during the first four weeks of life. Through the addition of 35 mg/animal nourseothricin to the feed effected after 4 weeks mast duration an improvement of the living mass development of about 25%; after the conclusion of 10 weeks mast test, this value amounts to a maximal 13%.

With regard to compatibility, nourseothricin mycelium has proven in animal tests to be non-toxic. Doses up to 5000 mg/kg body mass, delivered once by means of stomach tubes the male and female Wistar rats (body masses about 200 g), influence neither the body mass development of the test animals nor were sustenance-dependent mortalities observed.

OPERATIONAL EXAMPLES

EXAMPLE 12

For production of a nourseothricin-containing premix in the form of mycelium-containing bentonite-adsorbent, directly after the conclusion of fermentation, 0.1 liter formalin solution is added per 100 l culture solution, and stirred 15-30 minutes. Subsequently, 25% sulfuric acid is dosed in, until the acidity of pH 6.0 is obtained.

With corresponding chronological course, a bentonite suspension is pre-prepared in a stirrer vessel from acid- component material, by means of introducing 2 kg natrified bentonite into 15 liter water, and an addition of 0.2 liter of 25% sulfuric acid. The duration of soaking of the suspension must amount to at least 12 hours.

After the stirring in of the so-prepared bentonite suspension into the 100 liter culture solution (active substance content: 5000 mg nourseothricin per liter) as a rule a pH-value between 6.0 and 6.5 adjusts itself; if necessary, this pH-range can be adjusted through the addition of 25% sulfuric acid or 30% caustic soda. During the adsorption process, the reaction solution is continuously stirred. After at least 60 minutes reaction time, one can begin with the separation of solids, which can be performed through filtration or separation.

For such separation operations, particularly suitable is a vacuum rotary filter, which is to be prepared preliminarily, with appropriate chronology, by means of arranging a filter adjuvant layer of a specifically prepared calcium sulfate.

With an underpressure of $7 \cdot 10^4$ Pa, filtration efficiencies of 250 l/m²·h can be obtained. From 100 liter culture solution (=approximately 115 liters bentonite-culture solution-suspension), 93–98 liters filtrate are separated, with a residual active substance content corresponding to 5-10% of the starting activity.

The solids filtered off as intermediate products amounted to 12-14 kg with a residual moisture of 58-65%. With the filtration of 110-115 liters suspension, 2.0 to 2.5 kg filter adjuvant are consumed. The separated, moist solids are immediately conveyed to the drying stage. During the drying process, in a warm air stream, the product temperature of 70° C. cannot be exceeded. From 12 to 14 kg moist solids, 4.5–5.0 kg dry product with a nourseothricin-content of 75-85 g per kg dry substance are obtained. The active substance content was determined by means of the agar plate diffusion test, using Bacillus subtilis ATCC 6633 as test bacillus.

With the use of a ring stream drier, the dry product precipitates as finely grained, and can be used directly as premix for dosaging into the mixed feed agent. The product recovered by means of shelf, conveyor or fluidized bed driers, must be milled before the standardization or mixing in.

The dosaging of the mixed feed agent is so measured, that the nourseothricin content amounts to 5 to 100 mg per kg mixed feed agent dry substance.

The composition of the mixed feed agent determined for particular agricultural types of utilization and mast periods is compulsorily regulated through "Qualitätsanforderungen für Mischfuttermittel in der Tierproduktion".

EXAMPLE 13

For production of a nourseothricin-containing premix in the form of mycelium-containing dry product, the culture solution, as described in Example 12, is reacted directly after the completion of the fermentation with formalin, and adjusted to an acidity of pH 6.0 through dosaging of 25% sulfuric acid. Subsequently, the so-pretreated culture solution is compressed under gentle conditions in a suitable evaporator (vacuum rotating evaporator, underpressure $4 \cdot 10^4$ to $6 \cdot 10^4$ Pa, temperature 70° C.) and the concentrate is subsequently dried by means of a vacuum roller drier to a finely lumped solid product. During the drying process, running with an underpressure of $4 \cdot 10^4$ to $6 \cdot 10^4$ Pa, the material to be dried cannot be heated above 70° C.; the residual moisture of the dried end product must be smaller than 3%. From 100 liters culture solution with an original active substance content of 5000 mg/l nourseothricin, 3750 g mycelium-containing dry product with an active substance content of 113 mg nourseothricin per g dry substance are obtained.

The so-obtained mycelium-containing dry product is to be made before the standardization or mixing in.

The technique for the microbiological determination of the active substance content and the dosaging of mixed feed agents are the same as described in Example 12.

The advantages of the present invention are represented subsequently, with regard to its utility.

For a feeding test performed in ground maintenance, 400 unsorted broiler chicks (Tetra B) are distributed into said groups of 8 animals per group. Each treatment comprises 10 repeats. The average chick mass at the start of the test came to 38 g/animal. A broiler mast adjusted feed, corresponding to the DDR Quality Requirements 1980/81, was delivered to the animals, comprised of the following:
  64.5% corn groats
  21.0% soy extraction groats
  6.0% fish meal
  2.0% feed yeast
  3.0% rape
  2.5% mineral substance mixture for poultry with 54 g P/kg
  1.0% active substance premixture for broiler mass adjusted feed (antibiotic-free)

Feed rations for the test groups were supplemented with pure substance of nourseothricin-hydrochloride.

The effectiveness of staggered nourseothricin additions on the living mass development, the feed consumption and the feed expense, are represented in Tables 5, 6 and 7.

For a feeding test performed in battery maintenance, 3000 unsorted broiler chicks (Tetra B) are distributed into subgroups containing 100 animals per group. Each treatment involves 6 repeats. The average chick mass at the start of the test came to 37.5 g. The delivered feed had the same composition as set forth above. The feed rations for the test groups were supplemented with pure substance of nourseothricin-hydrochloride.

The effectiveness of staggered nourseothricin additions on the living mass development, the feed consumption and the feed expense, are set forth in Tables 8, 9 and 10.

For a feed test performed in ground maintenance, 55 piglets from cross-breeding actually employed in pig production, are distributed into subgroups containing 11 animals per group. The average living mass at the start of the tests came to 10.5 kg/animal.

The employed mixed feed agents had the following composition:
  Up to 40 kg living mass:
  45.0% wheat
  33.0% barley
  5.0% fish meal
  5.0% dry skimmed milk
  10.0% soy extraction groats
  1.0% mineral substance premixture with 50 g P/kg
  1.0% active substance pre-mixture for piglet breeding feed I (antibiotic-free)
  40 kg or more living mass:
  40.0% wheat
  48.0% barley
  7.0% soy extraction groats
  3.0% fish meal
  1.0% mineral substance pre-mixture with 35 g P/kg
  1.0% active substance pre-mixture for swine mast feed II (antibiotic-free)

The feed rations for the test groups were supplemented with pure substance of nourseothricin-hydrochloride, Kormogrisin or zinc bacitracin.

The effectiveness of staggered ergotropic-additions on the living mass development, the feed comsumption and the feed expense, are set forth in Tables 11, 12 and 13.

For two feeding tests performed in ground maintenance (Tests A and B), in each case 48 piglets from cross-breeding actually used in pig production, are distributed into subgroups containing 12 animals per group. The average living mass at the start of the tests came to 10.7 kg (Test A) or 12.6 kg (Test B).

The feed rations for the test groups were supplemented with a nourseothricin-premix in the form of mycelium-containing bentonite adsorbate.

The activity with regard to average living mass development, feed consumption and feed expense, determined in the course of each 7 days period, are set forth Tables 14, 15 and 16.

For a 10 week feeding test, 36 calves (black-colored milk cows) are distributed into subgroups containing 9 animals per group. The average living mass at the start of the tests came to 54 kg/animal.

The milk-substitution beverage contains per liter, 100 g of the milk substitute for calves, dissolved in water. This beverage was supplemented, directly before the delivery, with mycelium-containing nourseothricin-bentonite-adsorbate.

In addition, the animals received ad libitum a concentrate mixture of the following composition:
  30.0% wheat groats
  38.0% barley roats
  20.5% soy extraction groats
  4.0% sugar beet shreds, dried
  3.0% feed yeast, dried
  1.5% Mileipan (vitamin concentrate)
as well as the above described, corresponding daily to 0.5 kg Heu/animal.

The activity of staggered nourseothricin-additions with regard to animal health and living mass development of calves, is set forth in Table 13.

TABLE 1

Promotion of nourseothricin formation in agitation cultures of the stock *Streptomyces noursei* ZIMET 43716 through additions of sodium azide, pyrocatechol, amytal, zinc sulfate, β-alanine. Medium Bo-30

| | μg/ml nourseotricin | | | | |
|---|---|---|---|---|---|
| | sodium azide | pyrocatechol | amytal | zinc sulfate ($ZnSO_4.7H_2O$) | β-calanine |
| Concentration of the Additive (mM) | | | | | |
| 0.025 | 183 | — | — | — | — |
| 0.050 | 230 | — | — | — | — |
| 0.075 | 291 | — | — | — | — |

TABLE 1-continued

Promotion of nourseothricin formation in agitation cultures of the stock Streptomyces noursei ZIMET 43716 through additions of sodium azide, pyrocatechol, amytal, zinc sulfate, β-alanine, Medium Bo-30

μg/ml nourseotricin

| | sodium azide | pyrocatechol | amytal | zinc sulfate (ZnSO$_4$.7H$_2$O) | β-calanine |
|---|---|---|---|---|---|
| 0.100 | 330 | — | — | — | — |
| 0.125 | 458 | — | — | — | — |
| 0.150 | 544 | — | — | 388 | — |
| 0.175 | 372 | — | — | 399 | — |
| 0.200 | 230 | — | — | 440 | — |
| 0.250 | 224 | 263 | 185 | 469 | 210 |
| 0.500 | — | 277 | 221 | 560 | 329 |
| 0.750 | — | 294 | 228 | 702 | 311 |
| 1.00 | — | 396 | 291 | 552 | 258 |
| 1.25 | — | 412 | 301 | 439 | 255 |
| 1.50 | — | 382 | 206 | 437 | 212 |
| 1.75 | — | 250 | 174 | 124 | 157 |
| Without Additive (control): | | | 95 | | |

TABLE 2

Promotion of nourseothricin formation in agitation cultures of the stock Streptomyces noursei ZIMET 43716 through additions of sodium azide, pyrocatechol or zinc sulfate, Medium Bo-31

μg/ml nourseothricin

| | sodium azide | pyrocatechol | zinc sulfate (ZnSO$_4$.7H$_2$O) |
|---|---|---|---|
| Concentration of the Additive (mM) | | | |
| 0.050 | 961 | — | — |
| 0.100 | 1135 | — | — |
| 0.125 | 1426 | — | — |
| 0.150 | 1891 | — | — |
| 0.175 | 1085 | — | — |
| 0.200 | 657 | 941 | — |
| 0.300 | — | 1401 | 887 |
| 0.400 | — | 1984 | 1711 |
| 0.500 | — | 1166 | 1934 |
| 0.750 | — | 986 | 2158 |
| 1.00 | — | 868 | 2585 |
| 1.25 | — | 713 | 2604 |
| 1.50 | — | — | 2108 |
| 2.00 | — | — | 781 |
| Without Additive (control): | | 620 | |

TABLE 3

Nourseothricin content in laboratory fermentation cultures dosed with KH$_2$PO$_4$, glucose and (NH$_4$)$_2$SO$_4$ and non-dosed, of the stock Streptomyces noursei ZIMET 43716/NG13-14, in dependence on the fermentation period

| Fermentation period (h) | With Dosaging μg/ml | % | Without Dosaging (control) μg/ml | % |
|---|---|---|---|---|
| 24 | 1035 | 249 | 415 | 100 |
| 48 | 2980 | 165 | 1805 | 100 |
| 72 | 5412 | 294 | 1840 | 100 |
| 96 | 8311 | 213 | 3905 | 100 |
| 120 | 8800 | 195 | 4520 | 100 |
| 144 | 9230 | 213 | 4005 | 100 |

TABLE 4

Nourseothricin-content in 500 ml-fermenter cultures, both dosed with KH$_2$PO$_4$ and non-dosed, of the stock Streptomyces noursei ZIMET 43716/NG13-14 in dependence upon the fermentation time

| Fermentation period (h) | With Dosaging μg/ml | % | Without Dosaging (control) μg/ml | % |
|---|---|---|---|---|
| 20 | 225 | 216 | 104 | 100 |
| 44 | 1600 | 228 | 702 | 100 |
| 68 | 4858 | 299 | 1627 | 100 |
| 92 | 4903 | 208 | 2362 | 100 |
| 116 | 6862 | 191 | 3585 | 100 |
| 144 | 7781 | 200 | 3885 | 100 |

TABLE 5

Influence of staggered nourseothricin-additions on living development with broiler chicks in ground maintenance

| Nourseothricin-hydrochloride supplement (mg/kg) | Living mass 14$^{th}$ day (g) | (g) | Per Animal 28$^{th}$ day (g) | (g) | 52$^{th}$ day (g) | (g) |
|---|---|---|---|---|---|---|
| 0 | 200 | 100 | 525 | 100 | 1463 | 100 |
| 5.0 | 190 | 95 | 532 | 101 | 1469 | 100 |

TABLE 5-continued

Influence of staggered nourseothricin-additions on living development with broiler chicks in ground maintenance

| Nourseothricin-hydrochloride supplement (mg/kg) | Living mass 14th day (g) | (g) | Per Animal 28th day (g) | (g) | 52th day (g) | (g) |
|---|---|---|---|---|---|---|
| 10.0 | 208 | 104 | 548 | 104 | 1478 | 101 |
| 30.0 | 210 | 105 | 593 | 113 | 1548 | 106 |
| 50.0 | 214 | 107 | 588 | 112 | 1543 | 106 |
| $T_{0.05}$ | 14 | | 51 | | 77 | |

TABLE 6

Influence of staggered nourseothricin-additions on feed consumption with broiler chicks in ground maintenance

| Nourseothricin hydrochloride Supplement (mg/kg) | Feed Consumption/Animal 28th day (g) | (%) | 52th day (g) | (%) |
|---|---|---|---|---|
| 0 | 1105 | 100 | 3560 | 100 |
| 5.0 | 1087 | 98 | 3430 | 96 |
| 10.0 | 1183 | 107 | 3505 | 99 |
| 30.0 | 1146 | 104 | 3522 | 99 |
| 50.0 | 1100 | 100 | 3476 | 98 |

TABLE 7

Influence of staggered nourseothricin additions on the feed expense (1st to 52nd day) with broiler chicks in ground maintenance

| Nourseothricin hydrochloride Supplement | 0 | 5.0 | 10.0 | 30.0 | 50.0 |
|---|---|---|---|---|---|
| Feed Expense (kg/kg increase) | 2.5 | 2.4 | 2.4 | 2.3 | 2.3 |
| (%) | 100 | 96 | 96 | 92 | 92 |
| $T_{0.05}$ | | | 0.2 | | |

TABLE 8

Influence of staggered nourseothricin-additions on the living mass development with broiler chicks in battery maintenance

| Nourseothricin-hydrochloride Supplement (mg/kg) | 14th day (g) | (%) | Living Mass Per Animal 28th day (g) | (%) | 52th day (g) | (%) |
|---|---|---|---|---|---|---|
| 0 | 203 | 100 | 575 | 100 | 1477 | 100 |
| 20 | 196 | 97 | 594 | 103 | 1489 | 101 |
| 30 | 215 | 106 | 603 | 105 | 1567 | 106 |
| 40 | 219 | 108 | 614 | 108 | 1612 | 109 |
| 50 | 208 | 103 | 547 | 95 | 1544 | 105 |
| $T_{0.05}$ | | | 25 | | 114 | |

TABLE 9

Influence of staggered nourseothricin-additions on the feed consumption with broiler chicks in battery maintenance

| Nourseothricin-hydrochloride Supplement (mg/kg) | Feed Consumption Per Animal 28th day (g) | (%) | 52nd day (g) | (%) |
|---|---|---|---|---|
| 0 | 1131 | 100 | 3562 | 100 |
| 20 | 1186 | 105 | 3605 | 102 |
| 30 | 1157 | 102 | 3641 | 102 |
| 40 | 1048 | 93 | 3530 | 99 |
| 50 | 1061 | 94 | 3400 | 96 |

TABLE 10

Influence of staggered nourseothricin-additions on the feed expense (1st to 52nd mast day) with broiler chicks in battery maintenance

| Nourseothricin-hydrochloride Supplement (mg/kg) | 0 | 20 | 30 | 40 | 50 |
|---|---|---|---|---|---|
| Feed Expense (kg/kg increase) | 2.5 | 2.5 | 2.4 | 2.2 | 2.3 |
| (%) | 100 | 100 | 96 | 88 | 92 |

TABLE 11

Effectiveness of different ergotropics on the daily living mass development of pigs in ground maintenance

| Living Mass Segment (Ergotropicum) | 3–45 kg (g) | (%) | 45–120 kg (g) | (%) | 8–120 kg (g) | (%) |
|---|---|---|---|---|---|---|
| zinc bacitracin 120 mg/kg | 510 (82.8) | 105 | ./. | | | |
| zinc bacitracin 40 mg/kg | ./. | | 621 (86.0) | 101 | 581 (70.7) | 101 |
| Kormogrisin 40 mg/kg | 559 (61.3) | 115 | 578 (74.4) | 94 | 574 (49.8) | 101 |
| Nourseothricin-hydrochloride 10 mg/kg | 503 (57.8) | 104 | 602 (55.0) | 98 | 567 (40.2) | 100 |
| Nourseothricin-hydrochloride 40 mg/kg | 587 (36.6) | 121 | 617 (63.7) | 101 | 602 (47.7) | 106 |
| Control | 484 | 100 | 613 | 100 | 568 | 100 |

(numerical values in parentheses ≙ deviation of the measured value)

TABLE 12

Effectiveness of different ergotropics on the daily feed takeup with pigs in ground maintenance

| Living Mass Segment (Ergotropicum) | 8–45 kg (g) | (%) | 45–120 kg (g) | (%) | 8–120 kg (g) | (%) |
|---|---|---|---|---|---|---|
| zinc bacitracin 120 mg/kg | 1.33 | 95 | ./. | | 2.12 | 95 |
| zinc bacitracin 40 mg/kg | ./. | | 2.59 | 97 | | |
| Kormogrisin 40 mg/kg | 1.37 | 98 | 2.49 | 93 | 2.10 | 94 |
| Nourseothricin 10 mg/kg | 1.34 | 95 | 2.58 | 96 | 2.11 | 95 |
| Nourseothricin 40 mg/kg | 1.74 | 124 | 2.65 | 99 | 2.31 | 104 |
| Control | 1.40 | 100 | 2.67 | 100 | 2.94 | 100 |

TABLE 13

Effectiveness of different ergotropics on the feed take-up with pigs in ground maintenance (kg/kg increase)

| Living Mass Segment (Ergotropicum) | 8–45 kg (g) | (%) | 45–120 kg (g) | (%) | 8–120 kg (g) | (%) |
|---|---|---|---|---|---|---|
| zinc bacitracin 150 mg/kg | 2.61 | 90 | ./. | | 3.58 | 91 |
| zinc bacitracin 40 mg/kg | ./. | | 4.18 | 95 | | |
| Kormogrisin 40 mg/kg | 2.45 | 85 | 4.38 | 99 | 3.63 | 93 |
| Nourseothricin-hydrochloride 10 mg/kg | 2.66 | 92 | 4.28 | 97 | 3.74 | 95 |
| Nourseothricin-hydrochloride 40 mg/kg | 2.96 | 102 | 4.26 | 96 | 3.84 | 98 |

TABLE 13-continued

Effectiveness of different ergotropics on the feed take-up with pigs in ground maintenance (kg/kg increase)

| Living Mass Segment | 8–45 kg | | 45–120 kg | | 8–120 kg | |
|---|---|---|---|---|---|---|
| (Ergotropicum) | (g) | (%) | (g) | (%) | (g) | (%) |
| Control | 2.89 | 100 | 4.42 | 100 | 3.92 | 100 |

TABLE 14

Effectiveness of staggered nourseothricin-additions (mycelium adsorbate) on the average daily living mass increase (g/animal) with pigs in ground maintenance; test period 70 days

| | Control | | Nourseothricin - Active Substance | | | | | | (mg/kg feed) |
|---|---|---|---|---|---|---|---|---|---|
| | | | 7 | | 14 | | 21 | | |
| Test | (g) | (%) | (g) | (%) | (g) | (%) | (g) | (%) | |
| A | 479 | 100 | 496 | 104 | 548 | 114 | 580 | 123 | |
| | (104) | | (140) | | (41) | | (118) | | |
| B | 584 | 100 | 564 | 97 | 596 | 102 | 616 | 106 | |
| | (85) | | (92) | | (118) | | (507) | | |

(numerical values in parentheses = deviation of the measured values

TABLE 15

Effectiveness of staggered nourseothricin-additions (mycelium adsorbate) on the average daily feed take-up (kg feed/animal) with pigs in ground maintenance; test period 70 days

| | Control | | Nourseothricin Active Substance | | | | | | (mg/kg feed) |
|---|---|---|---|---|---|---|---|---|---|
| | | | 7 | | 14 | | 21 | | |
| Test | (g) | (%) | (g) | (%) | (g) | (%) | (g) | (%) | |
| A | 1.33 | 100 | 1.38 | 104 | 1.56 | 117 | 1.55 | 117 | |
| B | 1.72 | 100 | 1.66 | 97 | 1.62 | 94 | 1.68 | 98 | |

TABLE 16

Effectiveness of staggered nourseothricin-additions (mycelium adsorbate) on the average feed take-up (kg/kg increase) with pigs in ground maintenance; test duration 70 days

| | Control | | Nourseothricin Active Substance | | | | | | (mg/kg feed) |
|---|---|---|---|---|---|---|---|---|---|
| | | | 7 | | 14 | | 21 | | |
| Test | (g) | (%) | (g) | (%) | (g) | (%) | (g) | (%) | |
| A | 2.78 | 100 | 2.78 | 100 | 2.85 | 102 | 2.63 | 95 | |
| B | 2.94 | 100 | 2.94 | 100 | 2.73 | 93 | 2.73 | 93 | |

TABLE 17

Effectiveness of staggered nourseothricin-additions (mycelium adsorbate) on the animal health and the living mass development with calves (9 animals/group)

| Nourseothricin Active Substance (mg/animal/day) | 0.0 | 17.5 | 35.0 | 52.5 |
|---|---|---|---|---|
| starting mass | 55 | 53 | 53 | 55 |
| sickness days | 58 | 17 | 11 | 9 |
| variations | 1 | 0 | 0 | 0 |
| living mass development (g/animal/day) | | | | |
| 1st to 4th | | 488 | 552 | 611 | 587 |
| week of life | | (100%) | (113%) | (125%) | (120%) |
| 1st to 10th | | 663 | 708 | 742 | 729 |
| week of life | | (100%) | (107%) | (113%) | (110%) |

It will be understood that each of the elements described above, or two or more together, may also find a useful application in other types of fermentation differing from the types described above.

While the invention has been illustrated and described as embodied in a process for the production of nourseothricin and its adsorbate, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Process for the production of nourseothricin, its salts or adsorbate, comprising cultivation of nourseothricin-forming streptomycetes stock, streptomyces noursei ZIMET 43716 under submersed aerobic culture conditions in a suitable nutrient medium containing carbon and nitrogen sources and mineral salt, and subsequent isolation of the active substance, comprising adding to the nutrient medium water-soluble zinc salt, in a 0.2 to 1.75 milimolar concentration, β-alanine in a 0.25 to 1.75 milimolar concentration, alkali metal azide in a 0.05 to 0.25 milimolar concentration, pyrocatechol in a 0.20 to 1.75 milimolar concentration or ethyl isoamyl barbituric acid in a 0.25 to 1.75 milimolar concentration, performing a heat sterilization of the nutrient medium at a temperature from about 115°–125° C. in the presence of 0.10 to 1.75 milimolar concentration of a salt of zinc (II), iron (III), aluminum (III) or manganese (II), so that after conclusion of the sterilization a pH-value in the range from 7.2 to 8.8 is obtained, with or without addition of caustic soda before the sterilization, fermenting the main culture with a phosphate provision in a range from 0.1 up to 10 mg phosphate-phosphorus per liter medium per hour at a pH value from 5.0 to 6.5 over a period of 110–145 hours, at a fermentation temperature in the range from 26°–32° C., and with an oxygen partial pressure from 30 to 80%, as well as further substrate limitation to maintain a carbon-nitrogen ratio of 5 to 10 g glucose units to 0.015 to 0.2 g ammonium-nitrogen per liter medium, isolating the so-produced antibiotic by means of adsorption, eluting, concentrating, and then purifying, the antibiotic.

2. Process according to claim 1, wherein said fermenting is performed over a period of 120–130 hours.

3. The process according to claim 1, wherein said fermenting is performed at a temperature between 28°–30° C.

4. The process according to claim 1, wherein said oxygen partial pressure is maintained from 40 to 50%.

5. The process according to claim 1, wherein heat sterilization of the nutrient medium is performed in the presence of sulfate ions in a concentration from 0.05 up to 0.20 molar, in addition to calcium carbonate.

6. The process according to claim 1, wherein said adsorption of the antibiotic is performed with weakly acid cation exchange resin.

7. The process according to claim 1, wherein said antibiotic is adsorbed on bentonite.

8. The process according to claim 1, wherein after start of said fermenting, phosphate-containing substance is added to the fermentation continuously or at intervals.

9. The process according to claim 8, wherein said phosphate-containing substance comprises an aqueous solution of potassium dihydrogen phosphate.

10. The process according to claim 1, for the production of nourseothricin salt.

11. The process according to claim 10, wherein said nourseothricin salt is a salt of a polybasic acid.

* * * * *